United States Patent [19]

Arnott

[11] E Patent Number: Re. 33,039

[45] Reissued Date of Patent: Aug. 29, 1989

[54] LENS IMPLANT FOR INSERTION IN THE HUMAN EYE

[76] Inventor: Eric J. Arnott, 11-12 Milford House, 7 Queen Anne Street, London Win 9FD, England

[21] Appl. No.: 839,695

[22] Filed: Mar. 13, 1986

Related U.S. Patent Documents

Reissue of:

[64] Patent No.: 4,476,591
Issued: Oct. 16, 1984
Appl. No.: 528,337
Filed: Aug. 31, 1983

[30] Foreign Application Priority Data

Oct. 7, 1982 [GB] United Kingdom ..... 8228756

[51] Int. Cl.[4] ..... A61F 2/16
[52] U.S. Cl. ..... 623/6
[58] Field of Search ..... 623/6

[56] References Cited

U.S. PATENT DOCUMENTS

| | | | |
|---|---|---|---|
| 4,363,143 | 12/1982 | Callahan | 623/6 |
| 4,366,582 | 1/1983 | Faulkner | 623/6 |
| 4,435,855 | 3/1984 | Pannu | 623/6 |
| 4,494,254 | 1/1985 | Lopez | 623/6 |

FOREIGN PATENT DOCUMENTS

| | | | |
|---|---|---|---|
| 667206 | 6/1979 | U.S.S.R. | 623/6 |

OTHER PUBLICATIONS

American IOL International, Intraocular Lenses, (Advertisement).
American IOL International, 15542 Graham St., Huntington Beach, CA 92647, Style 130 & 130A Posterior Chamber Lenses, Dec. 29, 1981.
American Medical Optics Model PC-80, Posterior Chamber (Knolle).
Intraocular Lenses, (Advertisement), 4 pp., Sep. 1982, American Hospital Supply Corp., 1402 East Alton Ave., Irvine, CA 92714.
The Simcoe Posterior Chamber Lens, Feb. 1980, 4 pp.
CILCO, advertising brochure, The Single-Piece Perspex Posterior Chamber Lens, Mar. 1981, 2 pp.
"Guide to Small-incision IOLS" by Dianne Herrin, *Ocular Surgery News*, Nov. 15, 1988, vol. 6, No. 22, pp. 14 and 15. (RE 80.038).

*Primary Examiner*—Ronald L. Frinks
*Attorney, Agent, or Firm*—Brumbaugh, Graves, Donohue & Raymond

[57] ABSTRACT

A lens implant for insertion in the posterior chamber of human eye following an extra-capsular removal of the natural lens of the eye comprises a lens 1 of polymethyl methacrylate with two similar integral holding loops 2, which are flexible and resilient. Each loop 2 has a relatively stiff radial portion 3 followed by more flexible portions 5, 6 and 7 of varying curvatures. The free end 8 of each loop lies radially outwardly from the portion 5 of the other loop and the loops are so shaped that when the ends 8 are squeezed inwards into contact with the portion 5, the two loops 2 together form a substantially circular ring surrounding the lens concentrically. This facilitates insertion of the lens through an incision into the eye and, after insertion, the loops spring outwards again and engage either the anterior capsular flaps remaining after removal of the natural lens or the ciliary sulcus to hold the lens in position in the eye.

8 Claims, 1 Drawing Sheet

LENS IMPLANT FOR INSERTION IN THE HUMAN EYE

Matter enclosed in heavy brackets [ ] appears in the original patent but forms no part of this reissue specification; matter printed in italics indicates the additions made by reissue.

This invention relates to lens implants for insertion in the human eye from which the natural lens has been removed with an extra-capsular extraction.

Such lens implants consist of a lens made of polymethyl methyacrylate (PMMA) having holding portions projecting from its periphery to hold the lens in position in the eye between the posterior capsule and the iris after the implant has been inserted through an incision at the junction of the cornea and the sclera. The holding portions are usually in the form of closed loops or curved arms, which have one end free and are usually also known as loops, lying in the plane of the lens. The loops are flexible and resilient and in existing lens implants are of various shapes.

In most existing lens implants, the closed loops or curved arms are made of Prolene, which is a polypropylene and are fixed to the periphery of the lens. It has been found however that over a long period of time the Prolene is subject to some bio-degradation and if degradation takes place, there is a risk that the lens may become displaced in the eye unless sufficient fibrous growth has occured around it to hold it in place.

To overcome this problem attempts have been made to make the lens with integral holding portions of PMMA which is not subject to degradation. These integrally formed holding portions have been in the form of tabs which lie in the plane of the lens and project radially from its peripheryl. As these tabs are not able to bend in the plane of the lens in the same way as is possible with the loops or curved arms, they cannot spring outwards into contact with the internal surface of the eye after they have been inserted and for this reason they are not so successful as the loops or arms in holding the lens accurately in position in the eye. Further, also owing to the lack of flexibility in a radial direction in the plane of the lens, they tend to cause greater difficulities in the insertion of the implant through the incision in the eye than occur with implants having holding portions in the form of flexible loops or arms.

The aim of the present invention is to provide a lens implant for insertion in the posterior chamber of a human eye after an extra-capsular extraction, the implant comprising a lens with holding portions of PMMA so that the problem of degradation is overcome, and in which the holding portions are so formed that insertion into the eye is facilitated while the maintenance of the positioning of the implant in the eye is improved.

To this end, according to this invention, such a lens implant, which comprises a lens of PMMA with two similar holding loops or arms projecting from the periphery of the lens, each loop or arm lying substantially in the plane of the lens and being open-ended with one end fixed to the lens and the other end free, is characterised in that the loops or arms are of PMMA and each has one end formed integrally with the lens, the loops or arms being substantially diametrically opposite each other around the periphery of the lens, and each loop or arm, starting from the end which is integral with the lens, has a first portion extending substantially radially outwards from the lens, then extending around a sharp bend into a second portion of a curvature such that it follows, but is spaced radially outwards from, the periphery of the lens, a third portion which extends from, and is of less curvature than, the second portion, and a fourth portion which extends from the third portion and is of a greater curvature, substantially similar to that of the second portion, the end of the fourth portion being free and lying radially outwards of the second portion of the other loop or arm, so that the two loops or arms together surround the lens, and the first portion of each loop or arm being relatively stiff and the other portions being more flexible and resilient so that, in use, when the implant is to be inserted through an incision into the eye, the fourth portion of each loop or arm can be pressed inwards into contact with the second portion of the other loop or arm, and the two loops or arms bend in such a way that together they form a substantially circular ring surrounding the lens, and, after insertion, the loops or arms spring open again but the configuration of an encircling ring is maintained and the ring tends to adhere to the underlying posterior lens capsule although a part of it may encroach on to the ciliary sulcus. The encircling ring may act as a barrier protection against the ingrowth of secondary lens fibres from the fornix of the human lens. This will tend to prevent secondary clouding of the posterior capsule which normally occurs some months after the cataract extraction.

It has been found that by forming the lens with integral loops having the configuration, which is commonly known as a D-shape even though the straight part of the D is not present and the ends of the curved part of the D are not connected to each other, and also the relative stiffness of the different parts of the loops described above, the implant as a whole can be inserted through the incision in the eye and through the dilated iris into the posterior chamber more easily than can be done with existing forms of lens implant intended for insertion into the posterior chamber. After insertion, the shapes and flexibility of the loops or arms are such that the lens is held very securely in position regardless of whether the radially outer parts of the loops contact the anterior capsular flaps, which remain after removal of the anterior capsule, or the ciliary sulcus in between the posterior capsule and the iris.

The two loops or arms preferably lie in a flat plane which is the plane containing the periphery of the lens, but they may alternatively lie in the planes which are inclined to this plane by a small angle of up to 10° and it is this that is meant by saying that the loops or arms lie substantially in the plane of the lens.

Preferably each loop is of rectangular cross-section and of constant thickness perpendeicular to the plane of the lens. The first portion is then of greater width in this plane than the other portions to provide its greater stiffness. The width of the first portion tapers from the periphery of the lens to the beginning of the second portion and preferably the width of the second portion tapers from the first portion to the third portion. The third portion and the major part of the fourth portion are then preferably of constant width.

The width of the fourth portion of each loop is preferably increased at its free end and both the wider free end part and the first portion are preferably provided with positioning holes extending through them perpendicular to the plane of the lens.

These positioning holes assist in moving the lens into the exact required position after it has been inserted and, after insertion, material of the eye tends to grow and penetrate through the holes to anchor the lens implant more firmly in position.

The implant is preferably made, as is usual, of PMMA of CQ quality and in one example the material is PMMA CQ 6, which is manufactured by Imperial Chemical Industries Limited.

An example of a lens implant in accordance with the invention is illustrated in the accompanying drawings in which.

Figure 1:
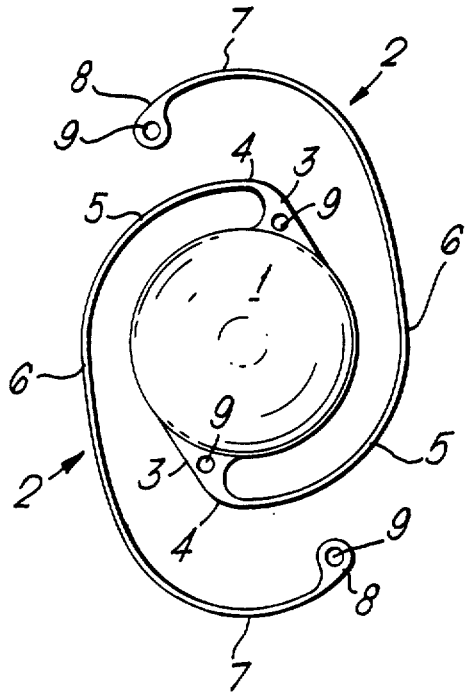
FIG. 1 is a front elevation of the implant.

The implant comprises a lens 1 and two holding loops 2 all of which are formed integrally with each other of PMMA CQ 6 quality. Each of the loops 2 has a first portion 3 which projects substantially radially from the periphery of the lens 1 and is of substantial width so that it is relatively stiff against bending in the plane of the lens 1. The first portion 3 is connected around a sharp bend 4 to a second portion 5 which has a curvature such that it is substantially concentric with the periphery of the lens 1. A third portion 6, the curvature of which is substantially less than that of the portion 5, extends from the portion 5 up to a fourth portion 7 which has the same curvature as the portion 5 so that the loop as a whole is almost symmetrical about an axis lying in the plane of the lens and perpendicular to the centre of the portion 6. The portion 7 has its tip 8 widened and a positioning hole 9 is formed in the widened tip 8. A second positioning hole 9 is formed in the portion 3.

As can be seen most easily from FIG. 1, the portions 3 of the two loops 2 are positioned diametrically opposite each other around the periphery of the lens 1 and in consequence the loops 2, which are the same as each other, are symmetrically disposed around the lens.

The portions 5, 6 and 7 are flexible and resilient so that when the loops 2 are bent in the plane of the lens with the portions 7 being pushed towards the periphery of the lens, the tip 8 of one loop will come into contact with the portion 5 of the other loop and the two loops taken together form a ring, which is of generally circular shape, extending around, but spaced from the periphery of the lens 1. The loops are squeezed inwards into these positions to enable the lens implant as a whole to be inserted into the posterior chamber of the eye in front of the posterior capsule.

Figure 2:
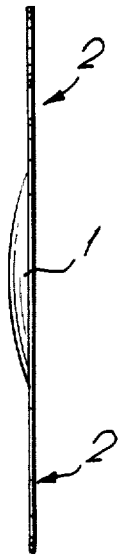
FIG. 2 is a side elevation as seen from the left-hand side of FIG. 1.

In this example, the lens 1, which is plano-convex as can be seen from FIG. 2, has a diameter of 5.5 mm. Both the loops 2 have a constant thickness of 0.14 mm perpendicular to the plane of the lens. The portion 5 of each loop has a width of 0.22 mm adjacent its junction with the portion 3 and the width tapers uniformly to 0.17 mm at the junction between the portions 5 and 6. The portions 6 and 7 have a constant width of 0.17 mm up to the widened tip 8. The positioning holes 9 have a diameter of 0.4 mm. The maximum overall dimension of the lens implant, that is the height as seen in FIG. 1, is 13.5 mm and the minimum overall dimension, that is the width as seen in FIG. 1, is 8.0 mm.

I claim:

1. A lens implant for insertion in the posterior chamber of a human eye after an extra-capsular extraction, said implant comprising a lens [of polymethyl methacrylate] and first and second similar holding loops formed integrally with and projecting from the periphery of said lens, each of said loops lying substantially in the plane of said lens and being open-ended with one end of said loop integral with said lens and the other end of said loop free, said ends of said loops which are integral with said lens being substantially diametrically opposite each other around the periphery of said lens, and each of said loops, starting from said end which is integral with said lens, including a first portion extending substantially radially outwards from said lens, a sharp bend extending from said first portion, a second portion extending from said bend, said second portion being of a curvature such that [is] *it* follows, but is spaced radially outwards from, said periphery of said lens, a third portion which extends from, and is of less curvature than, said second portion, and a fourth portion which extends from said third portion and is of a curvature substantially similar to that of said second portion, the end of said fourth portion remote from said third portion being free and lying radially outwards of [said second portion of] the other of said loops, whereby said two loops together surround said lens, and said first portion of each of said loops being relatively stiff and the other portions of said loops being more flexible and resilient so that, in use, when said implant is to be inserted through an incision into a human eye, said fourth portion of each of said loops can be pressed inwards into contact with [the second portion of] the other of said loops, and both said loops bend in such a way that together they form a substantially circular ring surrounding said lens, and, after insertion, said loops spring open [again, but] *and* the configuration of an encircling ring is maintained and said ring tends to adhere to the underlying posterior lens capsule of said eye.

2. A lens implant as claimed in claim 1, in which said loops lie in a flat plane, said plane containing the periphery of said lens.

3. A lens implant as claimed in claim 1, in which each of said loops is of rectangular cross-section and of constant thickness perpendicular to said plane, said first portion of each of said loops being of greater width in said plane than said second, third and fourth portions to provide said relative stiffness of said first portion.

4. A lens implant as claimed in claim 3, in which the width of said first portion of each of said loops tapers from said periphery of said lens towards said second portion.

5. A lens implant as claimed in claim 3 or claim 4, in which the width of the second portion of each of said loops tapers from said first portion to said third portion, and said third portion and a major part of said fourth portion are of constant width.

6. A lens implant as claimed in claim 1, in which the width of said fourth portion of each of said loops is increased at said free end thereof to form a wider free end part of said fourth portion and both said wider end part of said fourth portion and said first portion include means defining positioning holes therethrough, said holes extending perpendicular to said plane.

*7. A lens implant as claimed in claim 1, wherein the implant is made of polymethyl methacrylate.*

*8. A lens implant as claimed in claim 1, wherein the fourth portion of each loop lies radially outward from the second portion of the other loop such that, in use, when the implant is to be inserted through an incision into a human eye, said fourth portion of each loop can be pressed inward into contact with the second portion of the other loop.*

* * * * *